US012595235B2

(12) United States Patent
Green et al.

(10) Patent No.: US 12,595,235 B2
(45) Date of Patent: Apr. 7, 2026

(54) PROCESS FOR PRODUCING 4,5-DIHYDRO-1H-PYRAZOLES AND INTERMEDIATES

(71) Applicant: Novo Nordisk A/S, Bagsvaerd (DK)

(72) Inventors: Jeremy Green, Waltham, MA (US); Stefan Mix, Belfast (GB); Vincent Brunet, Moira (IE); Gareth Brown, Antrim (IE); Drazen Pavlovic, Portadown (IE)

(73) Assignee: Novo Nordisk A/S, Bagsvaerd (DK)

( * ) Notice: Subject to any disclaimer, the term of this patent is extended or adjusted under 35 U.S.C. 154(b) by 673 days.

(21) Appl. No.: 17/917,137

(22) PCT Filed: Apr. 7, 2021

(86) PCT No.: PCT/CA2021/050459
§ 371 (c)(1),
(2) Date: Oct. 5, 2022

(87) PCT Pub. No.: WO2021/203195
PCT Pub. Date: Oct. 14, 2021

(65) Prior Publication Data

US 2023/0159464 A1 May 25, 2023

Related U.S. Application Data

(60) Provisional application No. 63/006,311, filed on Apr. 7, 2020.

(51) Int. Cl.
*C07D 231/06* (2006.01)

(52) U.S. Cl.
CPC ........ *C07D 231/06* (2013.01); *C07B 2200/07* (2013.01)

(58) Field of Classification Search
None
See application file for complete search history.

(56) References Cited

U.S. PATENT DOCUMENTS

| | | | |
|---|---|---|---|
| 9,765,031 | B2 | 9/2017 | Kunos et al. |
| 10,329,259 | B2 | 6/2019 | Kunos et al. |
| 2022/0227714 | A1 | 7/2022 | Alimardanov et al. |

FOREIGN PATENT DOCUMENTS

| | | | | |
|---|---|---|---|---|
| WO | WO-2005102342 | A1 * | 11/2005 | ........... A61K 31/428 |
| WO | 2009059264 | A1 | 5/2009 | |
| WO | 2014018695 | A1 | 1/2014 | |
| WO | 2014078309 | A1 | 5/2014 | |
| WO | 2016196646 | A1 | 12/2016 | |
| WO | 2020236411 | A1 | 11/2020 | |

OTHER PUBLICATIONS

"Acyl Groups", http://dx.doi.org/10.1351/goldbook.A00123, 2014, original source 1995 (Year: 2014).*

Matsugi et al., "1H NMR Determination of Absolute Configuration of 1- or 2-Aryl-Substituted Alcohols and Amines by Means of Their Diastereomers: Novel Separation Technique of Diastereomeric Derivatives of Pyridyl Alcohols by Extraction", Chemistry—A European Journal, Nov. 2002, vol. 8, No. 24, pp. 5551-5565.

Brueggemeier et al., Modeling-Based Approach Towards Quality by Design for the Ibipinabant API Step, Organic Process Research & Development, 2012, 16:567-576.

Iyer et al., Design, Synthesis, and Biological Evaluation of Novel, Non-Brain-Penetrant, Hybrid Cannabinoid CB1R Inverse Agonist/Inducible Nitric Oxide Synthase (iNOS) Inhibitors for the Treatment of Liver Fibrosis, Journal of Medicinal Chemistry, 2017, 60:1126-1141.

PCT International Search Report and Written Opinion, PCT/CA2021/050459, Jun. 15, 2021, 10 pages.

* cited by examiner

*Primary Examiner* — Noble E Jarrell
(74) *Attorney, Agent, or Firm* — Elizabeth A. Dingess-Hammond

(57) ABSTRACT

Described are processes for the manufacture of compounds containing a (S)-4,5-dihydro-1H-pyrazole ring. These processes include a chiral resolution step of an intermediate using selected chiral resolving agents. For example, the chiral resolving agents may be selected from (−)-quinine, (R)-phenethylamine, (S)-phenethylamine, (S)-1-naphthylethylamine, (R)-(−)-2-amino-3-methyl-1-butanol, (−)-cinchonidine, (−)-spartein, (R)-1-naphthylethylamine, D-arginine, L-lysine, (S)-(+)-2-pyrrolidinemethanol and (1R,2S)-(+)-cis-1-amino-2-indanol.

Formula I

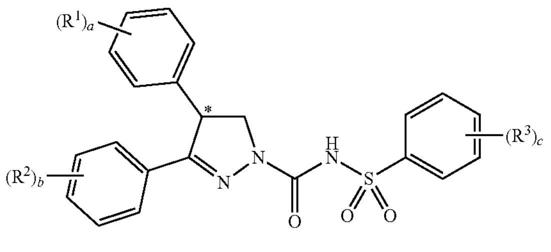

28 Claims, No Drawings

PROCESS FOR PRODUCING 4,5-DIHYDRO-1H-PYRAZOLES AND INTERMEDIATES

RELATED APPLICATION

The present application is the U.S. National Stage of PCT/CA2021/050459 with international filing date of Apr. 7, 2021, and which claims priority under applicable law to U.S. provisional application No. 63/006,311 filed on Apr. 7, 2020. The content of which each of the aforementioned applications is incorporated herein by reference in its entirety for all purposes.

TECHNICAL FIELD

This disclosure generally relates to processes for producing enantiomerically enriched substituted 4,5-dihydro-1H-pyrazoles and intermediates therefor.

BACKGROUND

It is generally known that activation of the cannabinoid $CB_1$ receptor increases appetite, increases the biosynthesis and storage of lipids, inhibits the actions of insulin and leptin, and promotes inflammation and fibrosis. Research was thus focused on developing $CB_1$ receptor inhibitors for the potential treatment of obesity and the metabolic disorder associated therewith, referred to as metabolic syndrome. Rimonabant was shown effective in treating metabolic syndrome but caused neuropsychiatric (i.e. CNS-related) side effects, which resulted in its withdrawal from the market.

Compounds preferentially targeting the $CB_1$ receptor in peripheral tissue (e.g. adipose tissue, liver, muscle, lung, kidney, macrophages, pancreatic beta cells and gastrointestinal tract), while not interacting with $CB_1$ receptors in brain tissue, thereby avoiding or reducing CNS-related side effects, were disclosed by George Kunos et al. in U.S. Pat. No. 9,765,031.

The compounds described in Kunos et al. all have at least one chiral center. Separation of the enantiomers of the final compound or of a synthetic intermediate is generally carried out by chiral chromatography (HPLC or SFC). Such methods would be either impractical or too expensive for large-scale production.

SUMMARY

According to a first aspect, the present technology relates to a process for the preparing an enantiomerically enriched compound, comprising the steps of:

(a) providing a compound of Formula I or a tautomer thereof:

Formula I

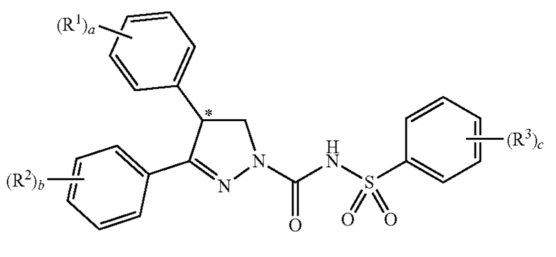

wherein, $R^1$, $R^2$, and $R^3$ are each independently selected from optionally substituted alkyl, optionally substituted cycloalkyl, optionally substituted heterocycloalkyl, halogen, cyano, nitro, hydroxy, optionally substituted alkoxy, amino, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino; and a, b, and c are each independently, 0, 1, 2, 3, 4 or 5;

wherein said compound of Formula I comprises a mixture of R and S isomers at the (*) carbon atom (C*) and wherein the fourth atom attached to C* is hydrogen or an isotope thereof (e.g. deuterium);

(b) dissolving the compound of Formula I in a solvent to obtain a solution;

(c) dissolving a chiral resolving agent selected from (−)-quinine, (R)-phenethylamine, (S)-phenethylamine, (S)-1-naphthylethylamine, (R)-(−)-2-amino-3-methyl-1-butanol, (−)-cinchonidine, (−)-spartein, (R)-1-naphthylethylamine, D-arginine, L-lysine, (S)-(+)-2-pyrrolidinemethanol, and (1R,2S)-(+)-cis-1-amino-2-indanol in the solution to form a precipitate and a supernatant; and (d) separating the precipitate from the supernatant, wherein one of the precipitate or the supernatant comprises the enantiomerically enriched compound comprising a higher concentration in S-enantiomer compared to the R-enantiomer of the compound of Formula I;

wherein steps (b) and (c) are carried out simultaneously or sequentially.

In one embodiment, the solvent is an aprotic organic solvent, e.g. acetonitrile. In an alternative embodiment, the solvent comprises an alcohol having from 1 to 4 carbon atoms, or a combination thereof, e.g. the alcohol is selected from ethanol, isopropanol, and a combination thereof (e.g. isopropanol). In one embodiment, the solvent further comprises water at a concentration of 10% or less, or 5% or less, or the solvent is anhydrous.

In another embodiment, the compound of Formula I is at a concentration of between about 50 g and about 150 g, or between about 75 g and about 120 g, or between about 85 g and about 115 g per liter of solvent in step (b).

In a further embodiment, step (c) comprises between about 0.5 and about 1, or between about 0.55 and about 0.75, or between about 0.6 and about 0.7, or about 0.65 molar equivalent of said chiral resolving agent with respect to the compound of Formula I.

In some embodiments, the chiral resolving agent is selected from (−)-quinine, (R)-phenethylamine, (S)-phenethylamine, (S)-1-naphthylethylamine, and (R)-(−)-2-amino-3-methyl-1-butanol, preferably, (−)-quinine. In these embodiments, the process may further comprise a step of treating the supernatant to obtain a solid enriched in (S) isomer of the compound of Formula I. In one embodiment, the step of treating comprises concentrating the supernatant by at least partial evaporation of the solvent. In another embodiment, the step of treating comprises adding an acidic aqueous solution to the supernatant, for example, the acidic aqueous solution has a pH comprised within the range of 0 to 1, preferably around 0. In a preferred embodiment, the volume ratio of the acidic aqueous solution to the total volume of solution is between 4% and 20%. In one embodiment, the acidic aqueous solution has a pH of about 0, and the volume ratio of the acidic aqueous solution to the total volume of solution is between 10% and 16%, or between 12% and 14%. In any of the foregoing embodiments, the process generally also further comprises a step of separating the solid from the supernatant after the treatment step.

In other embodiments, the chiral resolving agent is selected from (−)-cinchonidine, (−)-spartein, (R)-1-naphthylethylamine, D-arginine, L-lysine, (S)-(+)-2-pyrrolidinemethanol, and (1R,2 S)-(+)-cis-1-amino-2-indanol, for instance, (−)-spartein. In these embodiments, the process may further comprise recrystallizing the precipitate.

In a further embodiment, the process further comprises a step of separating the (S) isomer of the compound of Formula I from the chiral resolving agent, for instance, by addition of an acid (e.g. hydrochloric acid).

In yet another embodiment, the process further comprises recovering the (R) isomer of the compound of Formula I, at least partially racemizing said (R) isomer to obtain the compound of Formula I, and further treating said compound by steps (a) to (d).

In a further embodiment of the present process, the compound is of Formula I where a is zero, $R^1$ is absent, and $R^2$ and $R^3$ are each independently selected from halogenated alkyl and halogen, preferably b and c each being 1. In one embodiment, the compound is of Formula I(a) or I(b):

Formula I(a)

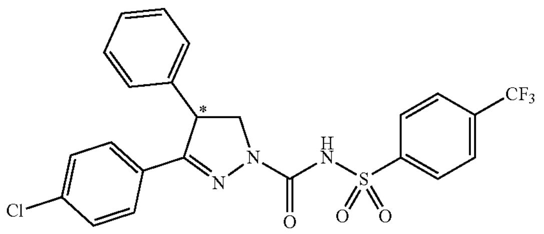

Formula I(b)

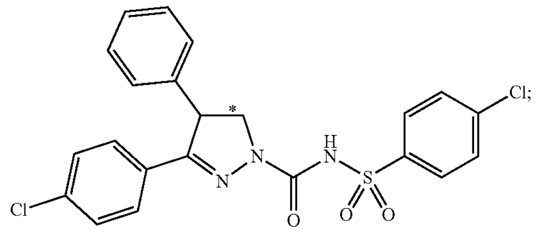

or a tautomer thereof.

According to another aspect, the present technology relates to a process for preparing a compound of Formula III, or a tautomer thereof:

Formula III

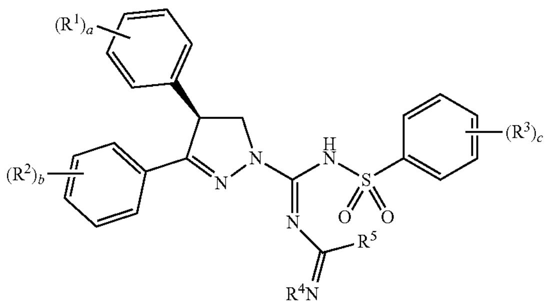

wherein, $R^1$, $R^2$, $R^3$, a, b, and c are as defined herein;

$R^4$ is selected from H, optionally substituted alkyl, optionally substituted cycloalkyl, optionally substituted heterocycloalkyl, halogen, cyano, nitro, hydroxy, optionally substituted alkoxy, amino, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino; and $R^5$ is selected from optionally substituted alkyl, optionally substituted cycloalkyl, optionally substituted heterocycloalkyl, halogen, cyano, nitro, hydroxy, optionally substituted alkoxy, amino, optionally substituted alkyl-C(O)NH, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino;

wherein the fourth atom attached to chiral carbon is hydrogen or an isotope thereof (e.g. deuterium);

the process comprising the steps of:

(i) preparing a compound of Formula II:

Formula II

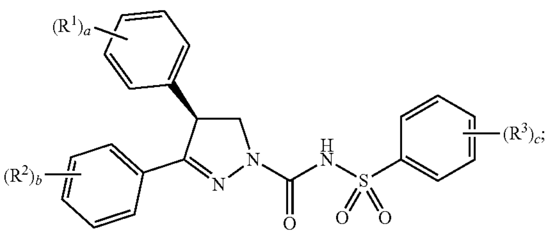

according to the process as defined above; and (ii) converting said compound of Formula II into the compound of Formula III.

In one embodiment, step (ii) comprises the steps of:

(ii-a) reacting the compound of Formula II with a chlorinating agent (e.g. $POCl_3$) to produce a compound of Formula IV:

Formula IV

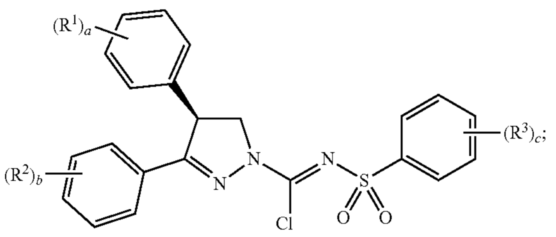

and (ii-b) reacting the compound of Formula IV with a compound of Formula V:

Formula V

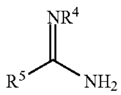

or a salt thereof, to produce the compound of Formula III.

In one embodiment, said step (ii-a) further comprises a base (e.g. 2,6-lutidine). In another embodiment, step (ii-b) further comprises a base (e.g. DBU, $K_2HPO_4$). In a further embodiment, a is zero and $R^1$ is absent, $R^2$ and $R^3$ are each independently selected from halogenated alkyl and halogen, preferably b and c each being 1. In a preferred embodiment, the compound of Formula III is selected from Compounds 1 to 26 as defined herein, or a tautomer thereof.

Additional objects and features of the present compound, compositions, methods and uses will become more apparent upon reading of the following non-restrictive description of exemplary embodiments and examples section, which should not be interpreted as limiting the scope of the invention.

DETAILED DESCRIPTION

All technical and scientific terms and expressions used herein have the same definitions as those commonly understood by a person skilled in the art to which the present technology pertains. The definition of some terms and expressions used is nevertheless provided below. To the extent the definitions of terms in the publications, patents, and patent applications incorporated herein by reference are contrary to the definitions set forth in this specification, the definitions in this specification will control. The section headings used herein are for organizational purposes only and are not to be construed as limiting the subject matter disclosed.

Chemical structures described herein are drawn according to conventional standards. Also, when an atom, such as a carbon atom, as drawn seems to include an incomplete valency, then the valency is assumed to be satisfied by one or more hydrogen atoms even though these are not necessarily explicitly drawn. Hydrogen atoms should be inferred to be part of the compound.

The terminology used herein is for the purpose of describing particular embodiments only and is not intended to be limiting. It should be noted that, the singular forms “a”, “an”, and “the” include plural forms as well, unless the content clearly dictates otherwise. Thus, for example, reference to a composition containing “a compound” also contemplates a mixture of two or more compounds. It should also be noted that the term “or” is generally employed in its sense including “and/or” unless the context clearly dictates otherwise. Furthermore, to the extent that the terms “including”, “includes”, “having”, “has”, “with”, or variants thereof are used in either the detailed description and/or the claims, such terms are intended to be inclusive in a manner similar to the term “comprising”.

The term “about” means within an acceptable error range for the particular value as determined by one of ordinary skill in the art, which will depend in part on how the value is measured or determined, i.e., the limitations of the measurement system. For example, “about” can mean within 1 or more than 1 standard deviation, per the practice in the art. Alternatively, “about” can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value. Where particular values are described in the application and claims, unless otherwise stated the term “about” meaning within an acceptable error range for the particular value should be assumed.

As used herein, the terms “compounds”, “active ingredient”, and equivalent expressions refer to compounds described in the present application and in U.S. Pat. No. 9,765,031 and PCT Patent Applications No. WO2009/059264 and No. WO2014/018695, including those encompassed by structural Formula I, optionally with reference to any of the applicable embodiments, and also includes exemplary compounds, such as Compounds 1 to 26, as well as their pharmaceutically acceptable salts, tautomeric forms, solvates, esters, and prodrugs when applicable. When a zwitterionic form is possible, the compound may be drawn as its neutral form for practical purposes, but the compound is understood to also include its zwitterionic form. Embodiments herein may also exclude one or more of the compounds. Compounds may be identified either by their chemical structure or their chemical name. In a case where the chemical structure and chemical name would conflict, the chemical structure will prevail.

The present compounds unless otherwise noted, also encompass all possible tautomeric forms of the illustrated compound, if any. The term also includes isotopically labeled compounds where one or more atoms have an atomic mass different from the atomic mass most abundantly found in nature. Examples of isotopes that may be incorporated into the present compounds include, but are not limited to, $^{2}H$ (D), $^{3}H$ (T), $^{11}C$, $^{13}C$, $^{14}C$, $^{15}N$, $^{18}O$, $^{17}O$, any one of the isotopes of sulfur, etc. The compounds may also exist in unsolvated forms as well as solvated forms, including hydrated forms. The compounds may exist in multiple crystalline or amorphous forms. However, amorphous or substantially amorphous forms are preferred for the formulations contemplated herein.

The chiral compounds and intermediates prepared by the present process may be substantially free of the corresponding enantiomer and may be enantiomerically enriched. “Enantiomerically enriched” means that the compound is made up of a significantly greater proportion of one enantiomer. In certain embodiments the compound is made up of at least about 60% by weight, or at least about 70% by weight, or at least about 80% by weight, or at least about 90% by weight of a preferred enantiomer. In other embodiments the compound is made up of at least about 95%, 98%, or 99% by weight of a preferred enantiomer. Preferred enantiomers may be isolated from racemic mixtures by any method known to those skilled in the art, including high-pressure liquid chromatography (HPLC) on chiral support and the formation and crystallization of chiral salts or be prepared by asymmetric syntheses.

The terms "ee", "% ee" and "enantiomeric excess" as used herein refer to the excess in one enantiomer for a chiral substance. For instance, a racemic mixture has a 0% ee, a pure enantiomer has a 100% ee, and a sample having 90% of S-isomer and 10% of R-isomer has a 80% ee in the S-isomer.

The expression "pharmaceutically acceptable salt" refers to those salts of the compounds of the present description which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the present description, or separately by reacting a free base function of the compound with a suitable organic or inorganic acid (acid addition salts) or by reacting an acidic function of the compound with a suitable organic or inorganic base (base-addition salts).

The term "solvate" refers to a physical association of one of the present compounds with one or more solvent molecules, including water and non-aqueous solvent molecules. This physical association may include hydrogen bonding. In certain instances, the solvate will be capable of isolation, for example when one or more solvent molecules are incorporated in the crystal lattice of a crystalline solid. The term "solvate" encompasses both solution-phase and isolable solvates. Exemplary solvates include, without limitation, hydrates, hemihydrates, alcoholates (e.g. ethanolates, hemiethanolates, n-propanolates, iso-propanolates, 1-butanolates, 2-butanolate, etc.), and solvates of other physiologically acceptable solvents, such as the Class 3 solvents described in the *International Conference on Harmonization (ICH), Guide for Industry, Q3C Impurities: Residual Solvents* (2017). Accordingly, the compound as herein described also includes each of its solvates and mixtures thereof.

The expression "pharmaceutically acceptable prodrugs" as used herein refers to those prodrugs of the compounds formed by the process of the present description which are, within the scope of sound medical judgment, suitable for use in contact with the tissues of humans and lower animals with undue toxicity, irritation, allergic response, and the like, commensurate with a reasonable benefit/risk ratio, and effective for their intended use. "Prodrug", as used herein means a compound which is convertible in vivo by metabolic means (e.g. by hydrolysis) to afford any compound delineated by the formulae of the instant description.

Abbreviations may also be used throughout the application, unless otherwise noted, such abbreviations are intended to have the meaning generally understood by the field. Examples of such abbreviations include Me (methyl), Et (ethyl), Pr (propyl), i-Pr (isopropyl), Bu (butyl), t-Bu (tert-butyl), i-Bu (iso-butyl), s-Bu (sec-butyl), c-Bu (cyclobutyl), Ph (phenyl), Bn (benzyl), Bz (benzoyl), CBz or Cbz or Z (carbobenzyloxy), Boc or BOC (tert-butoxycarbonyl), Su or Suc (succinimide), EtOH (ethanol), iPrOH or i-PrOH or IPA (isopropanol), MeCN (acetonitrile), EtOAc (ethyl acetate), DME (dimethoxyethane), MTBE (methyl tert-butyl ether), TFA (trifluoroacetic acid), and DBU (1,8-diazabicyclo [5.4.0]undec-7-ene).

The number of carbon atoms in a hydrocarbon substituent can be indicated by the prefix "$C_x$-$C_y$" or "$C_{x-y}$" where x is the minimum and y is the maximum number of carbon atoms in the substituent. However, when the prefix "$C_x$-$C_y$" or "$C_{x-y}$" is associated with a group incorporating one or more heteroatom(s) by definition (e.g. heterocycloalkyl, heteroaryl, etc), then x and y define respectively the minimum and maximum number of atoms in the cycle, including carbon atoms as well as heteroatom(s).

The term "alkyl" as used herein, refers to a saturated, straight- or branched-chain hydrocarbon radical typically containing from 1 to 20 carbon atoms. For example, "$C_1$-$C_8$ alkyl" contains from one to eight carbon atoms. Examples of alkyl radicals include, but are not limited to, methyl, ethyl, propyl, isopropyl, n-butyl, tert-butyl, neopentyl, n-hexyl, heptyl, octyl radicals and the like.

The term "alkenyl" as used herein, denotes a straight- or branched-chain hydrocarbon radical containing one or more double bonds and typically from 2 to 20 carbon atoms. For example, "$C_{2-8}$ alkenyl" contains from two to eight carbon atoms. Alkenyl groups include, but are not limited to, for example, ethenyl, propenyl, butenyl, 1-methyl-2-buten-1-yl, heptenyl, octenyl and the like.

The term "alkynyl" as used herein, denotes a straight- or branched-chain hydrocarbon radical containing one or more triple bonds and typically from 2 to 20 carbon atoms. For example, "$C_{2-8}$ alkynyl" contains from two to eight carbon atoms. Representative alkynyl groups include, but are not limited to, for example, ethynyl, 1-propynyl, 1-butynyl, heptynyl, octynyl and the like.

The terms "cycloalkyl", "alicyclic", "carbocyclic" and equivalent expressions refer to a group comprising a saturated or partially unsaturated (non-aromatic) carbocyclic ring in a monocyclic or polycyclic ring system, including spiro (sharing one atom), fused (sharing at least one bond) or bridged (sharing two or more bonds) carbocyclic ring systems, having from three to fifteen ring members. Examples of cycloalkyl groups include, without limitation, cyclopropyl, cyclobutyl, cyclopentyl, cyclopenten-1-yl, cyclopenten-2-yl, cyclopenten-3-yl, cyclohexyl, cyclohexen-1-yl, cyclohexen-2-yl, cyclohexen-3-yl, cycloheptyl, bicyclo[4,3,0]nonanyl, norbornyl, and the like. The term cycloalkyl includes both unsubstituted cycloalkyl groups and substituted cycloalkyl groups. The term "$C_3$-$C_n$cycloalkyl" refers to a cycloalkyl group having from 3 to the indicated "n" number of carbon atoms in the ring structure. Unless the number of carbons is otherwise specified, "lower cycloalkyl" groups as herein used, have at least 3 and equal or less than 8 carbon atoms in their ring structure.

As used herein, the terms "heterocycle", "heterocycloalkyl", "heterocyclyl", "heterocyclic radical", and "heterocyclic ring" are used interchangeably and refer to a chemically stable 3- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 1-3 heteroatoms selected from oxygen, sulfur or nitrogen, the nitrogen may be N (as in 3,4-dihydro-2H-pyrrolyl), NH (as in pyrrolidinyl), or NR (as in N-substituted pyrrolidinyl). A heterocyclic ring can be attached to its pendant group at any heteroatom or carbon atom that results in a chemically stable structure and any of the ring atoms can be optionally substituted. Examples of heterocycloalkyl groups include, but are not limited to, 1,3-dioxolanyl, pyrrolidinyl, pyrrolidonyl, pyrazolinyl, pyrazolidinyl, 4,5-dihydropyrazolyl, imidazolinyl, imidazolidinyl, piperidinyl, piperazinyl, oxazolidinyl, isoxazolidinyl, morpholinyl, thiazolidinyl, isothiazolidinyl, tetrahydrofuranyl, tetrahydropyranyl, tetrahydrothiopyranyl, tetrahydrodithienyl, tetrahydrothienyl, thiomorpholino, thioxanyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, 2H-pyranyl, 4H-pyranyl, dioxanyl, dithianyl, dithiolanyl, dihydropyranyl, dihydrothienyl, dihydrofuranyl, 3-azabicyclo[3,1,0]hexanyl, 3-azabicyclo[4,1,0]heptanyl, quinolizinyl, quinuclidinyl, tetrahydroquinolinyl, tetrahydroisoquinolinyl, decahydroquinolinyl, and the like. Heterocyclic groups also include groups in which a heterocyclic ring is fused to one or more aryl, heteroaryl, or cycloaliphatic rings, such as indolinyl, 3H-indolyl, chromanyl, chromenyl, phenanthridinyl, 2-azabicyclo[2.2.1]heptanyl, octahydroindolyl, or tetrahydroquinolinyl, where the radical or point of attachment is on the heterocyclyl ring. A heterocyclyl group may be mono- or bicyclic. The term "heterocyclylalkyl" refers to an alkyl group substituted by a heterocyclyl, wherein the alkyl and heterocyclyl portions independently are optionally substituted. The term "$C_{3-n}$heterocycloalkyl" refers to a heterocycloalkyl group having from 3 to the indicated "n" number of atoms in the ring structure, including carbon atoms and heteroatoms.

As used herein, the term "partially unsaturated" refers to a ring moiety that includes at least one double or triple bond between ring atoms but is not aromatic. The term "partially unsaturated" is intended to encompass rings having multiple sites of unsaturation but is not intended to include aryl or heteroaryl moieties, as herein defined.

The term "aryl" used alone or as part of a larger moiety as in "aralkyl", "aralkoxy", "aryloxy", or "aryloxyalkyl", refers to aromatic groups having 4n+2 conjugated π(pi) electrons, wherein n is an integer from 1 to 3, in a monocyclic moiety or a bicyclic or tricyclic fused ring system having a total of six to 15 ring members, wherein at least one ring in the system is aromatic and wherein each ring in the system contains three to seven ring members. The term "aryl" may be used interchangeably with the term "aryl ring". In certain embodiments of the present description, "aryl" refers to an aromatic ring system which includes, but not limited to, phenyl, biphenyl, naphthyl, azulenyl, anthracyl and the like, which may bear one or more substituents. The term "aralkyl" or "arylalkyl" refers to an alkyl residue attached to an aryl ring. Examples of aralkyl include, but are not limited to, benzyl, phenethyl, and the like. Also included within the scope of the term "aryl", as it is used herein, is a group in which an aromatic ring is fused to one or more non-aromatic rings, such as indanyl, indenyl, phthalimidyl, naphthimidyl, fluorenyl, phenanthridinyl, or tetrahydronaphthyl, and the like. The term "$C_{6-n}$ aryl" refers to a aryl group having from 6 to the indicated "n" number of atoms in the ring structure.

The term "heteroaryl", used alone or as part of a larger moiety, e.g., "heteroaralkyl", or "heteroaralkoxy", refers to aromatic groups having 4n+2 conjugated π(pi) electrons, wherein n is an integer from 1 to 3 (e.g. having 5 to 18 ring atoms, preferably 5, 6, or 9 ring atoms; having 6, 10, or 14 π electrons shared in a cyclic array); and having, in addition to carbon atoms, from one to five heteroatoms. The term "heteroatom" includes but is not limited to nitrogen, oxygen, or sulfur, and includes any oxidized form of nitrogen or sulfur, and any quaternized form of a basic nitrogen. A heteroaryl may be a single ring, or two or more fused rings. The term "heteroaryl", as used herein, also includes groups in which a heteroaromatic ring is fused to one or more aryl, cycloaliphatic, or heterocyclic rings, where the radical or point of attachment is on the heteroaromatic ring. Nonlimiting examples of heteroaryl groups include thienyl, furanyl (furyl), pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, triazinyl, indolyl, 3H-indolyl, isoindolyl, indolizinyl, benzothienyl(benzothiophenyl), benzofuranyl, dibenzofuranyl, indazolyl, benzimidazolyl, benzoxazolyl, benzothiazolyl, benzotriazolyl, pyrrolopyridinyl (e.g. pyrrolo[3,2-b]pyridinyl or pyrrolo[3,2-c]pyridinyl), pyrazolopyridinyl (e.g. pyrazolo[1,5-a]pyridinyl), furopyridinyl, purinyl, imidazopyrazinyl (e.g. imidazo[4,5-b]pyrazinyl), quinolyl(quinolinyl), isoquinolyl(isoquinolinyl), quinolonyl, isoquinolonyl, cinnolinyl, phthalazinyl, quinazolinyl, quinoxalinyl, 4H-quinolizinyl, naphthyridinyl, and pteridinyl carbazolyl, acridinyl, phenanthridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. Heteroaryl groups include rings that are optionally substituted. The term "heteroaralkyl" refers to an alkyl group substituted by a heteroaryl, wherein the alkyl and heteroaryl portions independently are optionally substituted. Examples include, but are not limited to, pyridinylmethyl, pyrimidinylethyl and the like. For instance, the term "$C_{5-n}$ heteroaryl" refers to a heteroaryl group having from 5 to the indicated "n" number of atoms in the ring structure, including carbon atoms and heteroatoms.

The term "halogen" designates a halogen atom, i.e. a fluorine, chlorine, bromine or iodine atom, preferably fluorine or chlorine.

As described herein, compounds of the present description may contain "optionally substituted" moieties. In general, the term "substituted", whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at each position. Combinations of substituents envisioned under the present description are preferably those that result in the formation of chemically stable or chemically feasible compounds. The term "chemically stable", as used herein, refers to compounds that are not substantially altered when subjected to conditions to allow for their production, detection, and, in certain embodiments, their recovery, purification, and use for one or more of the purposes disclosed herein.

The term "optionally substituted" thus refers to groups that are substituted or unsubstituted by independent replacement of one, two, or three or more of the hydrogen atoms thereon with substituents including, but not limited to F, Cl, Br, I, OH, $CO_2H$, alkoxy, oxo, thiooxo, $NO_2$, CN, $CF_3$, $NH_2$, NHalkyl, NHalkenyl, NHalkynyl, NHcycloalkyl, NHaryl, NHheteroaryl, NHheterocyclic, dialkylamino, diarylamino, diheteroarylamino, O-alkyl, O-alkenyl, O-alkynyl, O-cycloalkyl, O-aryl, O-heteroaryl, O-haloalkyl, O-heterocyclic, C(O)alkyl, C(O)alkenyl, C(O)alkynyl, C(O)cycloalkyl, C(O)aryl, C(O)heteroaryl, C(O)heterocycloalkyl, $CO_2$alkyl, $CO_2$alkenyl, $CO_2$alkynyl, $CO_2$cycloalkyl, $CO_2$aryl, $CO_2$heteroaryl, $CO_2$heterocycloalkyl, OC(O)alkyl, OC(O)alkenyl, OC(O)alkynyl, OC(O)cycloalkyl, OC(O)aryl, OC(O)heteroaryl, OC(O)heterocycloalkyl, C(O)$NH_2$, C(O)NHalkyl, C(O)NHalkenyl, C(O)NHalkynyl, C(O)NHcycloalkyl, C(O)NHaryl, C(O)NHheteroaryl, C(O)NHheterocycloalkyl, $OCO_2$alkyl, $OCO_2$alkenyl, $OCO_2$alkynyl, $OCO_2$cycloalkyl, $OCO_2$aryl, $OCO_2$heteroaryl, $OCO_2$heterocycloalkyl, OC(O)$NH_2$, OC(O)NHalkyl, OC(O)NHalkenyl, OC(O)NHalkynyl, OC(O)NHcycloalkyl, OC(O)NHaryl, OC(O)NHheteroaryl, OC(O)NHheterocycloalkyl, NHC(O)alkyl, NHC(O)alkenyl, NHC(O)alkynyl, NHC(O)cycloalkyl, NHC(O)aryl, NHC(O)heteroaryl, NHC(O)heterocycloalkyl, $NHCO_2$alkyl, $NHCO_2$alkenyl, $NHCO_2$alkynyl, $NHCO_2$cycloalkyl, $NHCO_2$aryl, $NHCO_2$heteroaryl, $NHCO_2$heterocycloalkyl, NHC(O)$NH_2$, NHC(O)NHalkyl, NHC(O)NHalkenyl, NHC(O)NHalkenyl, NHC(O)NHcycloalkyl, NHC(O)NHaryl, NHC(O)NHheteroaryl, NHC(O)NHheterocycloalkyl, NHC(S)$NH_2$, NHC(S)NHalkyl, NHC(S)NHalkenyl, NHC(S)NHalkynyl, NHC(S)NHcycloalkyl, NHC(S)NHaryl, NHC(S)NHheteroaryl, NHC(S)NHheterocycloalkyl, NHC(NH)$NH_2$, NHC(NH)NHalkyl, NHC(NH)NHalkenyl, NHC(NH)NHalkenyl, NHC(NH)NHcycloalkyl, NHC(NH)NHaryl, NHC(NH)NHheteroaryl, NHC(NH)NHheterocycloalkyl, NHC(NH)alkyl, NHC(NH)alkenyl, NHC(NH)alkenyl, NHC(NH)cycloalkyl, NHC(NH)aryl, NHC(NH)heteroaryl, NHC(NH)heterocycloalkyl, C(NH)NHalkyl, C(NH)NHalkenyl, C(NH)NHalkynyl, C(NH)NHcycloalkyl, C(NH)NHaryl, C(NH)NHheteroaryl, C(NH)NHheterocycloalkyl, S(O)alkyl, S(O)alkenyl, S(O)alkynyl, S(O)cycloalkyl, S(O)aryl, $S(O)_2$alkyl, $S(O)_2$alkenyl, $S(O)_2$alkynyl, $S(O)_2$cycloalkyl, $S(O)_2$aryl, S(O)heteroaryl, S(O)heterocycloalkyl, $SO_2NH_2$, $SO_2$NHalkyl, $SO_2$NHalkenyl, $SO_2$NHalkynyl, $SO_2$NHcycloalkyl, $SO_2$NHaryl, $SO_2$NHheteroaryl, $SO_2$NHheterocycloalkyl, $NHSO_2$alkyl, $NHSO_2$alkenyl, $NHSO_2$alkynyl, $NHSO_2$cycloalkyl, $NHSO_2$aryl, $NHSO_2$heteroaryl, $NHSO_2$heterocycloalkyl, $CH_2NH_2$, $CH_2SO_2CH_3$, alkyl, alkenyl, alkynyl, aryl, arylalkyl, heteroaryl, heteroarylalkyl, heterocycloalkyl, cycloalkyl, carbocyclic, heterocyclic, polyalkoxyalkyl, polyalkoxy, methoxymethoxy, methoxyethoxy, SH, S-alkyl, S-alkenyl, S-alkynyl, S-cycloalkyl, S-aryl, S-heteroaryl, S-heterocycloalkyl, or methylthiomethyl.

The present compounds are intermediates in the synthesis of peripherally restricted CB1 antagonists. These compounds include a chiral center on the dihydropyrazole ring. The S isomers have been identified as most often more potent compared to the R counterpart. Efforts have thus been directed to the identification of a scalable process for separating the isomers either of the final product or of an intermediate thereof. However, attempts of enantiomeric resolution by crystallization of diastereomeric salts of the final product, for instance Compound 1 below, were unsuccessful.

Examples of final compounds that could be produced using the present process are as defined in U.S. Pat. No. 9,765,031, and PCT Patent Applications No. WO2009/059264 and No. WO2014/018695, all incorporated herein by reference in their entirety for all purposes, and including those defined herein in the following paragraphs. When referring to chemical moieties, the recitation of a listing of chemical groups in any definition of a variable includes definitions of that variable as any single group or combination of listed groups. Similarly, the recitation of an embodiment herein includes that embodiment as any single embodiment or in combination with any other embodiments or portions thereof. As such, the following embodiments are present alone or in combination if applicable.

More specifically, the present document relates to a process for preparing enantiomerically enriched compounds comprising a dihydropyrazole ring. For instance, the process comprises the steps of:

(a) providing a compound of Formula I or a tautomer thereof:

Formula I

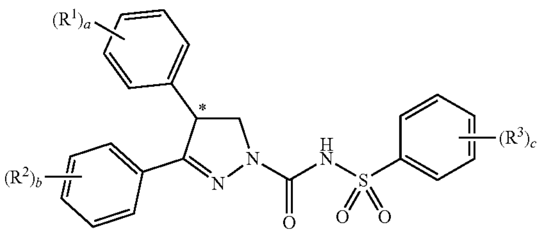

wherein, $R^1$, $R^2$, and $R^3$ are each independently selected from optionally substituted alkyl, optionally substituted cycloalkyl, optionally substituted heterocycloalkyl, halogen, cyano, nitro, hydroxy, optionally substituted alkoxy, amino, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino; and a, b, and c are each independently, 0, 1, 2, 3, 4 or 5;

wherein said compound of Formula I comprises a mixture of R and S isomers at the (*) carbon atom (C*) and wherein the fourth atom attached to C* is hydrogen or an isotope thereof (e.g. deuterium);

(b) dissolving the compound of Formula I in a solvent to obtain a solution;

(c) dissolving a chiral resolving agent selected from (−)-quinine, (R)-phenethylamine, (S)-phenethylamine, (S)-1-naphthylethylamine, (R)-(−)-2-amino-3-methyl-1-butanol, (−)-cinchonidine, (−)-spartein, (R)-1-naphthylethylamine, D-arginine, L-lysine, (S)-(+)-2-pyrrolidinemethanol, and (1R,2S)-(+)-cis-1-amino-2-indanol in the solution to form a precipitate and a supernatant; and (d) separating the precipitate from the supernatant, wherein one of the precipitate or the supernatant comprises the enantiomerically enriched compound comprising a higher concentration in S-enantiomer compared to the R-enantiomer of the compound of Formula I;

wherein steps (b) and (c) are carried out simultaneously or sequentially.

The solvent used is an organic solvent which may be protic or aprotic and may further include water. The solvent preferably comprises at least one lower alcohol, for example selected from alcohol having from 1 to 4 carbon atoms (e.g. ethanol and isopropanol), or a combination thereof. Other solvents include aprotic organic solvent such as acetonitrile. The solvent may also further comprise water (e.g. less than 10% v/v, or 5% v/v or less) or may be used without addition of water.

Depending on the chiral resolving agent used, the S-enantiomer enriched compound may be present in the supernatant. Examples of such chiral resolving agents include (−)-quinine, (R)-phenethylamine, (S)-phenethylamine, (S)-1-naphthylethylamine, and (R)-(−)-2-amino-3-methyl-1-butanol, preferably (−)-quinine. When one of these is used, the supernatant is further treated to obtain a solid which is enriched in (S) isomer of the compound of Formula I which is further separated from the supernatant. Such a treatment may include concentrating the supernatant by at least partial evaporation of the solvent (e.g. by heating and/or vacuum), by addition of an acidic aqueous solution to the supernatant, for instance having a pH within the range of 0 to 1, preferably around 0, or by a combination of partial evaporation and acidic treatment.

Where the acidic treatment is used, the volume ratio of the acidic aqueous solution to the total volume of solution is between 4% and 20%. For instance, the acidic aqueous solution has a pH of about 0, and the volume ratio of the acidic aqueous solution to the total volume of solution is between 10% and 16%, or between 12% and 14%.

In other cases, the S-enantiomer enriched compound may be present in the precipitate of step (c). Examples of such chiral resolving agents include (−)-cinchonidine, (−)-spartein, (R)-1-naphthylethylamine, D-arginine, L-lysine, (S)-(+)-2-pyrrolidinemethanol, and (1R,2S)-(+)-cis-1-amino-2-indanol, preferably (−)-spartein. The precipitate may then be further treated after isolation to increase its S-enantiomeric content, for instance by recrystallization.

The above process also further comprises a step of separating the enantiomerically-enriched compound of Formula I from the chiral resolving agent which was used for the resolution. Acidification is generally used for such a separation. For instance, an acid, such as hydrochloric acid, can be used to form a salt with the chiral resolving agent, which preferably remains in solution while the free enantiomerically enriched compound precipitates.

The resulting enantiomerically enriched compound is made up of at least about 60% by weight, or at least about 70% by weight, or at least about 80% by weight, or at least about 90% by weight of S-enantiomer. Preferably, the compound is made up of at least about 95%, 98%, or 99% by weight of S-enantiomer.

The process may also further comprise recovering the (R) isomer of the compound of Formula I, at least partially racemizing said (R) isomer to obtain the compound of Formula I, and further treating said compound by steps (a) to (d) above to afford additional isomer (S) of the compound of Formula I. For example, such a racemization can be carried out in the presence of an organic base such as DBU.

It is understood that the S-enantiomer of the compound of Formula I is a compound of Formula II, or a tautomer thereof:

Formula II

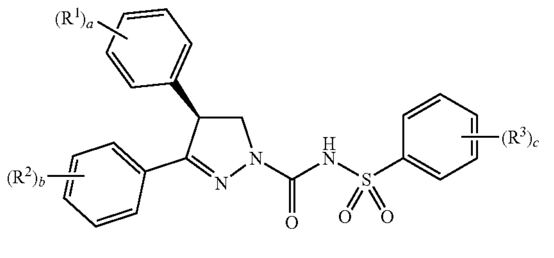

In some instances of Formula I or II, a is 0 and $R^1$ is absent, i.e. all five free carbon atoms of the aryl group being linked to a hydrogen atom. Preferably, b is 1 and $R^2$ is halogen and/or c is 1 and $R^3$ is halogen (e.g. chlorine) or halogenated $C_{1-6}$alkyl, e.g. trifluoromethyl. For instance, a is zero, $R^1$ is absent, and $R^2$ and $R^3$ are each independently selected from halogenated alkyl and halogen, preferably b and c each being 1.

According to one example, the compound of Formula I is a compound of Formula I(a) or I(b), or a tautomer thereof:

Formula I(a)

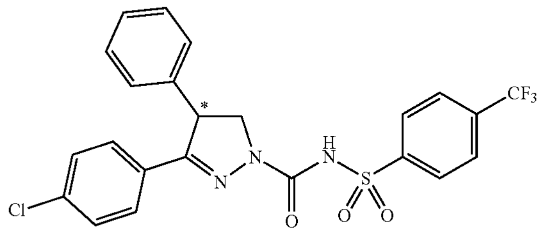

Formula I(b)

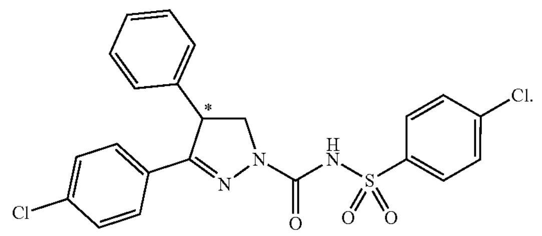

According to another example, the compound of Formula II is a compound of Formula II(a) or II(b), or a tautomer thereof:

Formula II(a)

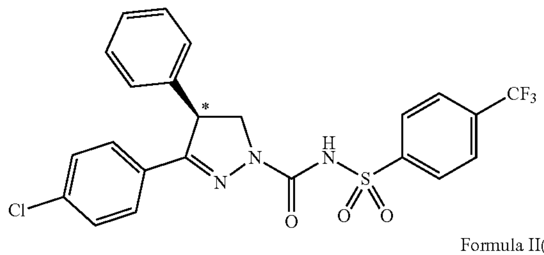

Formula II(b)

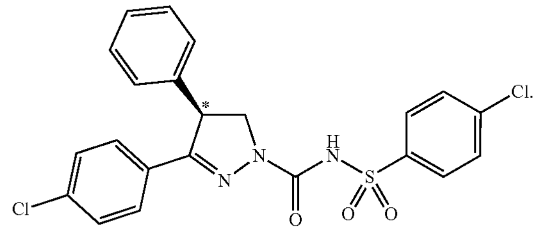

While the present document describes the isolation of the (S)-enantiomer of a compound of Formula I, it is understood that the (R)-enantiomer would be isolated using the procedure described herein with a chiral resolving agent having the reverse chirality of that disclosed. Examples of chiral resolving agents of reverse chirality include (+)-quinine, (R)-1-naphthylethylamine, (R)-phenethylamine, (S)-phenethylamine, (S)-(−)-2-amino-3-methyl-1-butanol, (+)-cinchonidine, (+)-spartein, (S)-1-naphthylethylamine, L-arginine, D-lysine, (R)-(−)-2-pyrrolidinemethanol, (1S,2R)-(−)-cis-1-amino-2-indanol, etc. For instance, the synthesis of (+)-quinine has been previously described (see for example, S. Shiomi et al., *Chem. Sci.,* 2019, 10, 9433).

The compounds of Formula I may generally be prepared by the reaction of an $(R^3)_c ArSO_2NH_2$ compound (A) with ClC(O)OMe in basic conditions to afford an $(R^3)_c ArSO_2NHC(O)OMe$ intermediate (B), which is then coupled with a free amine (C) of the formula:

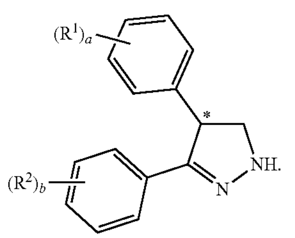

The present technology also further relates to a process for the manufacture of a S-dihydropyrazole ring-containing compound, such as $CB_1$ receptor inhibitors as defined above, such as the compound (S)-Ibipinabant or a compound of Formula III below.

For instance, the process comprises (i) preparing a compound of Formula II according to the above process, and (ii) converting the compound of Formula II into a compound of Formula III, or a tautomer thereof:

Formula III

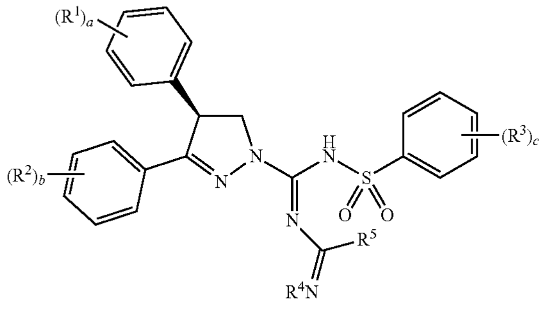

wherein, $R^1$, $R^2$, $R^3$, a, b, and c are as defined above;

$R^4$ is selected from H, optionally substituted alkyl, optionally substituted cycloalkyl, optionally substituted heterocycloalkyl, halogen, cyano, nitro, hydroxy, optionally substituted alkoxy, amino, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino; and $R^5$ is selected from optionally substituted alkyl, optionally substituted cycloalkyl, optionally substituted heterocycloalkyl, halogen, cyano, nitro, hydroxy, optionally substituted alkoxy, amino, optionally substituted alkylC(O)NH, optionally substituted sulfonyl, optionally substituted aryl, optionally substituted heteroaryl, optionally substituted carboxyl, acyl, optionally substituted alkenyl, optionally substituted alkynyl, optionally substituted phosphonyl, optionally substituted phosphinyl, optionally substituted boronate, optionally substituted silyl, and imino.

Step (ii) may comprise the steps of:

(ii-a) reacting the compound of Formula II with a chlorinating agent to produce a compound of Formula IV:

Formula IV

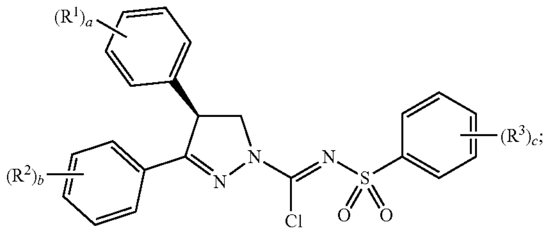

and (ii-b) reacting the compound of Formula IV with a compound of Formula V:

Formula V

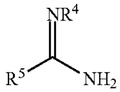

or a salt thereof, to produce the compound of Formula III.

An example of a chlorinating agent is $POCl_3$ and step (ii-a) preferably further comprises an organic base like 2,6-lutidine. Step (ii-b) also preferably further comprises a base, e.g. an organic base such as 1,8-diazabicyclo[5.4.0]undec-7-ene (DBU), or an inorganic base such as $K_2HPO_4$.

In some examples, $R^4$ is H. In other examples, $R^5$ is $C_{1-6}$alkyl (e.g. methyl) or $C_{1-6}$alkylC(O)NH (e.g. $CH_3C(O)NH$).

Alternatively, the compound of Formula IV is reacted with an amine of formula $R^4NH_2$ to produce a compound as defined in PCT Patent Application No. WO2009/059264 or No. WO2014/018695. Non-limiting examples of compounds of Formula III include the following Compounds 1 to 26:

Compound 1

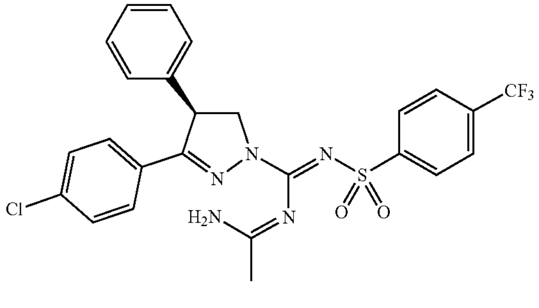

-continued
Compound 2
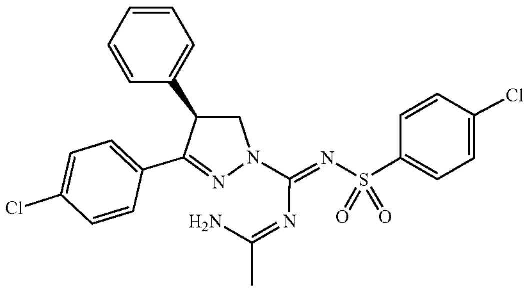
Compound 3
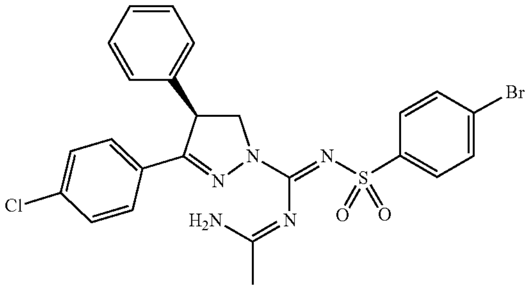
Compound 4
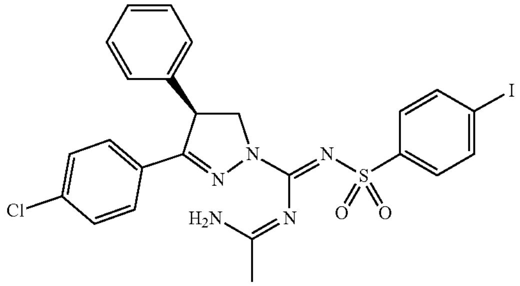
Compound 5
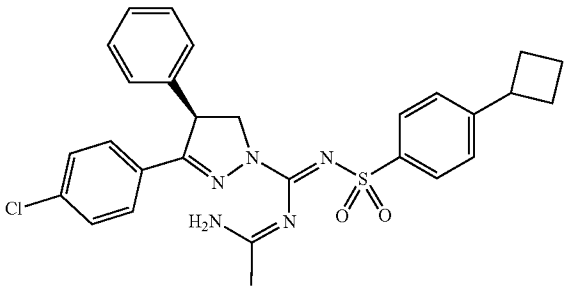
Compound 6
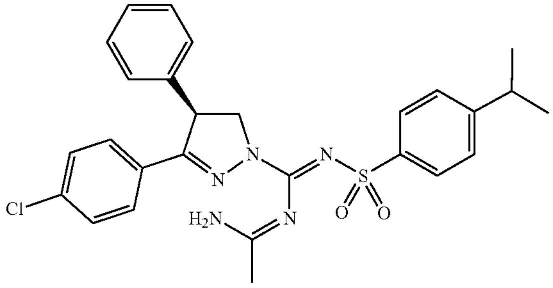
-continued
Compound 7
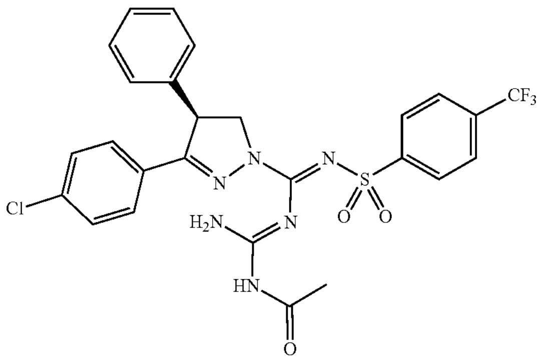
Compound 8
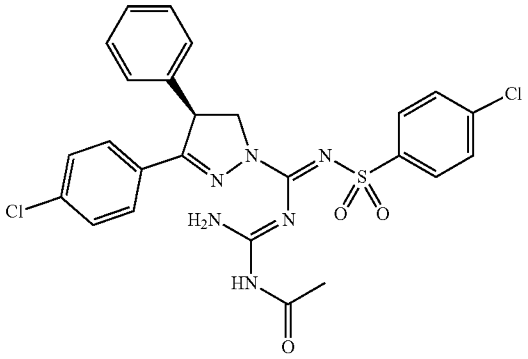
Compound 9
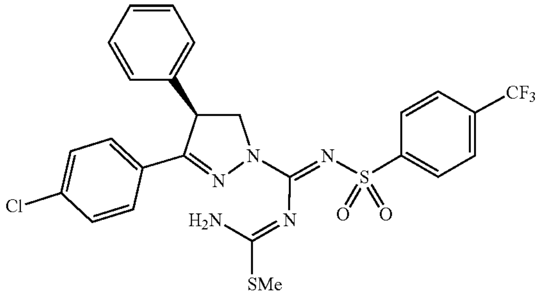
Compound 10
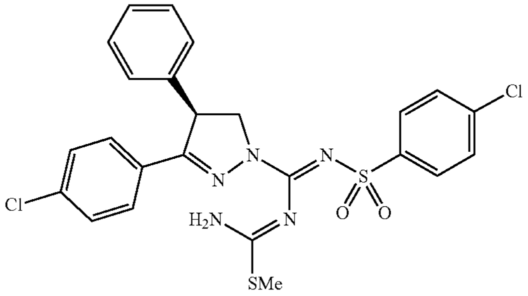

-continued
Compound 11
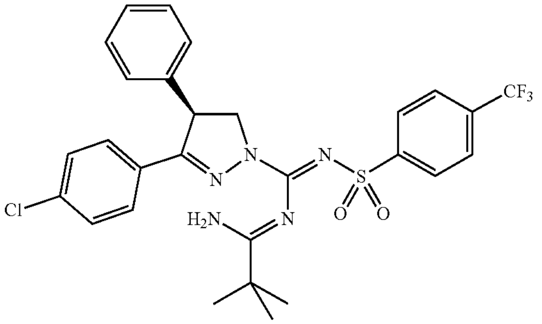
Compound 12
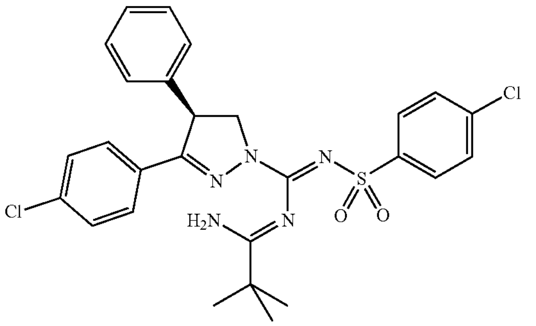
Compound 13
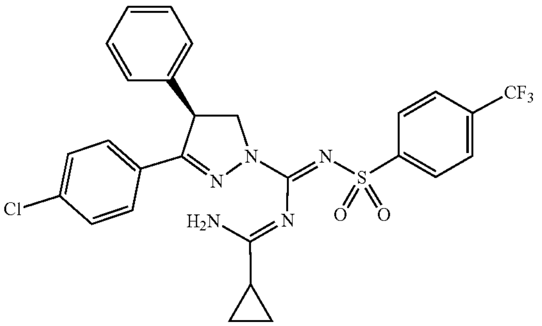
Compound 14
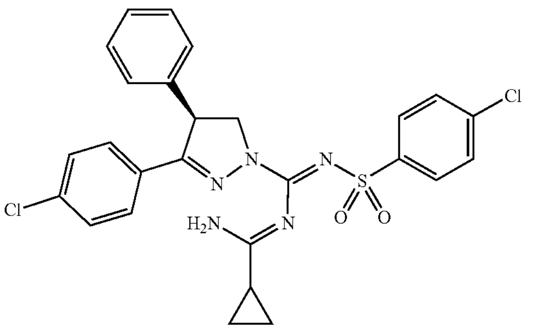
-continued
Compoound 15
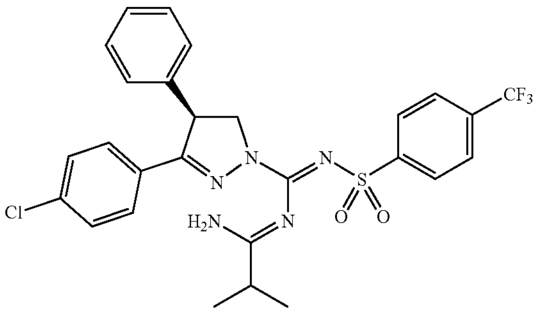
Compound 16
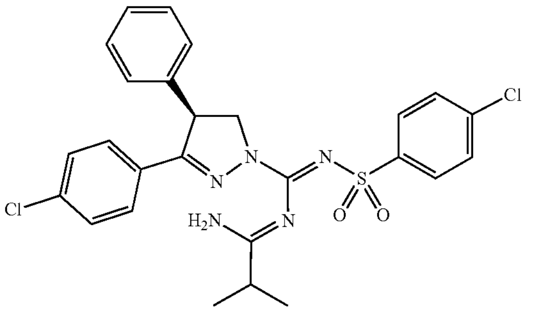
Compound 17
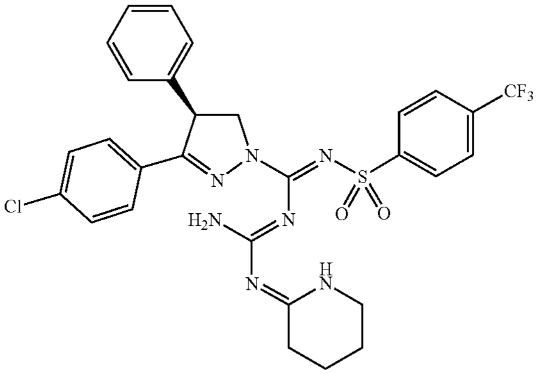
Compound 18
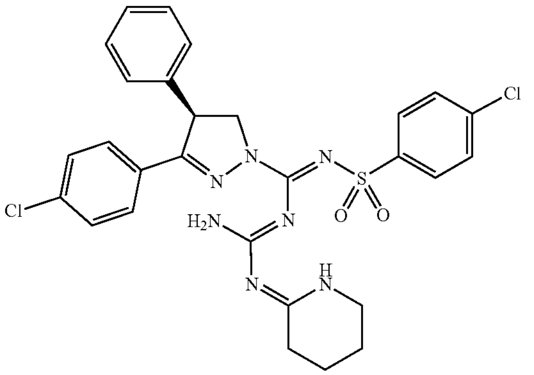

Compound 19
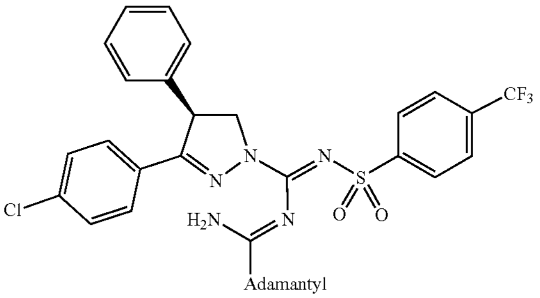
Compound 20
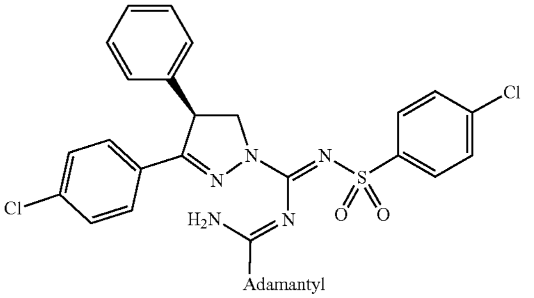
Compound 21
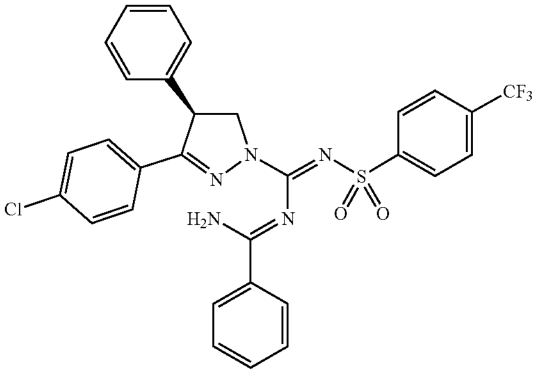
Compound 22
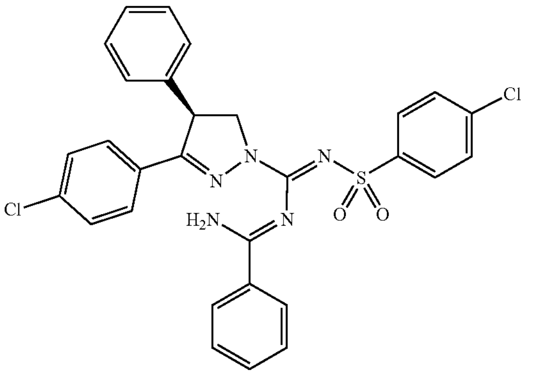
Compound 23
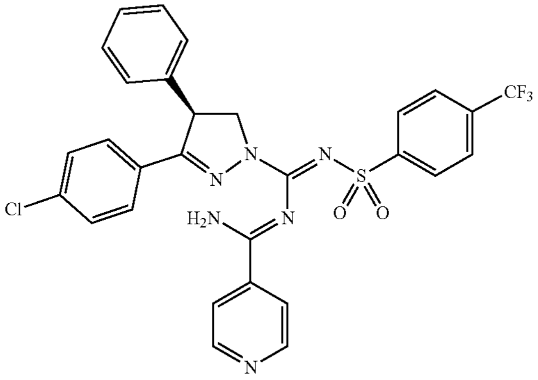
Compound 24
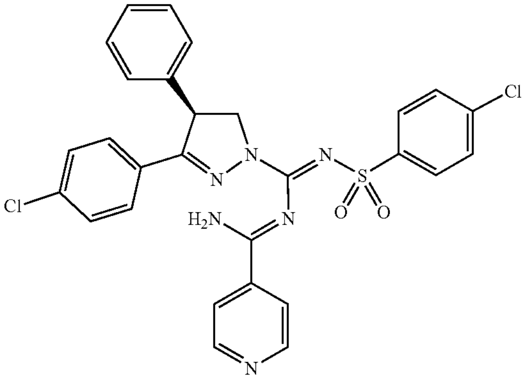
Compound 25
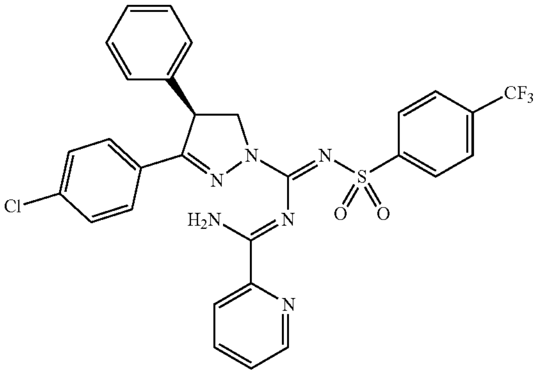
Compound 26
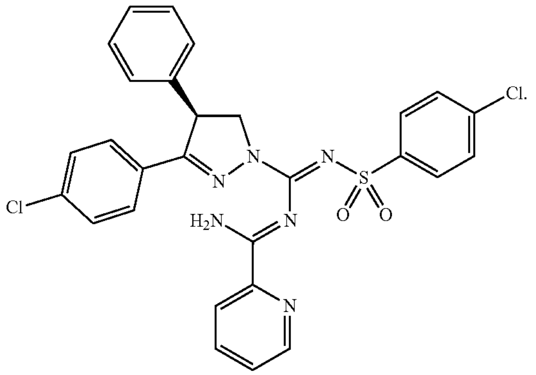
The recitation of an embodiment for a variable herein includes that embodiment as any single embodiment or in combination with any other embodiments or portions thereof. The recitation of an embodiment herein includes that embodiment as any single embodiment or in combination with any other embodiments or portions thereof.

EXAMPLES

The following non-limiting examples are illustrative embodiments and should not be construed as further limiting the scope of the present invention. These examples will be better understood with reference to the accompanying figures.

Unless otherwise indicated, all numbers expressing quantities of ingredients, reaction conditions, concentrations, properties, stabilities, and so forth used in the specification and claims are to be understood as being modified in all instances by the term "about." At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

Example 1—Enantiomeric Resolution with Various Chiral Resolving Agents (Formula I(a))

A racemic mixture or substantially racemic mixture of the compound of Formula I(a):

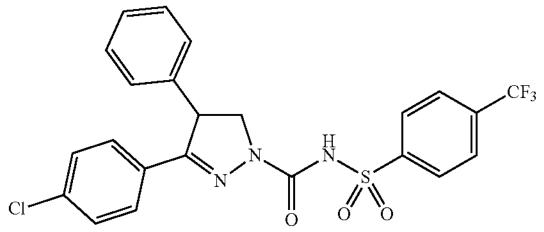

was dissolved in three different solvents (isopropanol, isopropanol:water 95:5 v/v, and ethanol:water 95:5 v/v) together with a chiral base compound as resolving agent. Resolving agents are commercially available while the compound of Formula I(a) was prepared by known methods.

Screening experiments were carried out at microscale in 4 mL glass vials by addition of equimolar amounts of the compound of Formula I(a) (0.5 mmol, 1 equiv.) and resolving agent (0.5 mmol, 1 equiv.). Then, calculated amount of solvent was added to each vial to give 23% w/w solution based on theoretical weight of diastereoisomeric salt formed and the resulting suspension was heated until a clear solution or a reasonably clear mixture was obtained. The vials were then shaken at room temperature in an orbital shaker at 95 rpm over two days to induce crystallization.

Close to 30 different resolving agents were tested. In experiments where no crystal formation was observed, up to 4 different treatments (if necessary) were applied (i.e. cooling to −20° C., sonication at room temperature, slow evaporation of solvent at room temperature, solvent evaporation under vacuum at 50° C.) to trigger crystal formation. Results for the resolving agents showing the presence of a solid and enrichment in S-enantiomer (in the solid or supernatant) are shown in Table 1.

TABLE 1

Selected screening results

| Resolving agent | Solvent[a] | % ee supernatant | % ee solid |
|---|---|---|---|
| (−)-quinine | A | 72.2(S) | 83.4(R) |
| (−)-quinine | B | 40.2(S) | 41.2(R) |
| (−)-quinine | C | 94.6(S) | 26.7(R) |
| (−)-quinine | D | 69(S) | 92(R) |
| (−)-cinchonidine | B | 0 | 9.8(S) |
| (−)-spartein | B | 44.2(R) | 32.8(S) |
| (−)-spartein | C | 85.4(R) | 17.0(S) |
| (R)-phenethylamine | B | 16.6(S) | n/a[b] |
| (S)-phenethylamine | B | 16.4(S) | n/a[b] |
| (R)-1-naphthylethylamine | B | 6.4(R) | 11.8(S) |
| (S)-1-naphthylethylamine | B | 4.2(S) | 6.2(R) |
| D-arginine | B | 0 | 3.9(S) |
| L-lysine | B | 0 | 6.3(S) |
| (R)-(−)-2-amino-3-methyl-1-butanol | B | 23.8(S) | 18.8(R) |
| (S)-(+)-2-pyrrolidinemethanol | B | 0 | 16.0(S) |
| (1R, 2S)-(+)-cis-1-amino-2-indanol | C | 4.8(R) | 2.7(S) |

[a]Solvent A: 95% EtOH/water; B: 95% i-PrOH/water; C: iPrOH; D: MeCN;
[b]n/a: data not available due to no solid formation (or oil formed).

Among those tested, (−)-quinine and (−)-spartein displayed some potential as resolution agents (liquor composition #50:50) in the 3 different solvents tested. In all 3 solvents (−)-quinine showed moderate-high enantioenrichment of S-enantiomer in the liquors while the R-enantiomer was present in the solid. (−)-Spartein in IPA and IPA/water 95:5 v/v displayed low-moderate enantioenrichment in S-enantiomer in the crystals. Some other chiral resolving agents also showed enrichment in the desired S isomer in the crystal or mother liquor.

Example 2—Optical Resolution in Isopropanol (Formula I(a))

Additional testing was carried out using (−)-quinine to determine the optimum amount of solvent and scale conditions to be used during resolution.

Repetition of screening experiment with the compound of Formula I(a) and (−)-quinine in IPA was carried out at 17.7 mmol scale (9.0 g Formula I(a)). To carry out the crystallisation, the reaction mixture was subjected to several heating cooling cycles in the range of 40-70° C., and after the last cycle cooled down gradually to ambient temperature under stirring with seeding using diastereomeric salt crystals 85% ee in R-enantiomer. Reaction mixture was stirred for about 18 hours at room temperature.

A sample was then taken from the reaction mixture and composition of mother liquors and solid was determined by chiral HPLC (Phenomenex Lux™ i-amylose-1 column, 40° C., isocratic elution with IPA/Hexane/TFA 99:1:0.1 v/v/v). % ee in mother liquors displayed 34.4% ee in (S). Since calculated eutectic 77.5% ee (S) was not achieved in liquors (34.4% ee was determined by chiral HPLC) slurry was vacuum filtered to afford 2.17 g of diastereoisomeric salt (87.4% ee solid; determined by chiral HPLC). Mother liquor was evaporated to ⅓ of the initial volume (54 g of IPA solution) followed by seeding with R-diastereoisomeric salt (85% ee in R-enantiomer) at 40° C. Reaction was left stirring overnight at room temperature. After 14 hours of stirring a sample was taken from the reaction mixture to determine the composition of mother liquor and solid by chiral HPLC (42.2% ee of S in the mother liquor). Reaction mixture was again vacuum filtered, and the resulting mother liquor concentrated to about 60% of the initial volume (34 g) followed by seeding with R-diastereoisomeric salt (85% ee in R-enantiomer) at 40° C. Reaction was left stirring at RT over the weekend (76 hours). The composition of mother liquor and solid was determined by chiral HPLC (45.7% ee in mother liquor).

The reaction was repeated on a 4 g scale giving 49.3% ee of S-enantiomer in mother liquor after overnight stirring at room temperature. Following vacuum filtration of the reaction mixture mother liquor was evaporated to half the initial volume (39.9 g of IPA solution) and the resulting mixture seeded with R-diastereoisomeric salt (85% ee in R-enantiomer) at 40° C. Reaction was left stirring for 76 hours at room temperature. Composition of mother liquor and solid was determined by chiral HPLC (61.5% ee in the mother liquor).

A subsequent reaction was carried out on a 2 g scale with a slight alteration of reaction conditions. The initial phase of the reaction was carried out at 70° C. until a clear solution was observed (about 10 min). A solution was then cooled down to room temperature (a precipitate started to appear) and stirred for additional 1 h 20 min. The reaction was diluted with 20 mL IPA and refluxed for 10 min at 70° C. followed by addition of additional IPA (20 mL). A suspension was again cooled down to room temperature followed by addition of 20 mL IPA. The suspension was stirred for 15 min and then filtered through an S3 sintered funnel. After IPA wash, HPLC analysis showed the crystals to have an ee 85.3% (R) while liquor % ee was 72.4 (S). Reaction on a 2 g scale was repeated following the above procedure and the suspension was left stirring overnight (18 h). HPLC analysis revealed the crystals with ee 64.8% (R); liquor was 85.6% ee (S). Diastereoisomeric salt (85.6% ee) was decomposed by addition of 2M aq. HCl followed by filtration of the obtained precipitate on a sinter funnel (porosity 3) to afford S-enantiomer (99.4% ee).

Example 3—Optical Resolution and Further Enrichment in Acetonitrile (Formula I(a))

(a) Chiral Resolution

A 50 g scale reaction was carried out in a reactor using the compound of Formula I(a) and (−)-quinine. More specifically, 50 g of the compound of Formula I(a), 20.76 g of (−)-quinine (0.65 eq.) and 443 g of HPLC grade acetonitrile (MeCN, about 564 mL) were mixed in the reactor and the temperature raised to 65° C. for 30 minutes. The mixture was then cooled to 20° C. over a period of 4.5 hours and was maintained at 15° C. overnight (about 18 hours). The slurry was then filtered. The crystals included 95.8% (ee) of the R-isomer while the mother liquors provided 77.2% (ee) of the S-isomer.

(b) Enrichment of S-Isomer

The mother liquor from step (a) comprising the S-isomer enriched solution was further treated to improve the enantiomeric excess (ee) of the S-isomer. The volume of the mother liquor was adjusted to 400 mL (69.25 g/L Formula I(a)) and half of the solution was used for an ee improvement assays. Ten fractions of 20 mL were collected, each of them containing 1.38 g pyrazoline. Each 20 mL aliquot was treated with various volumes of acidic water at pH 1 or 0 (see Table 2). After overnight stirring in MeCN/water, the solids were filtered and analysed by HPLC and NMR.

TABLE 2

HPLC results for % ee improvement assays

| Water pH 1 added (mL) | Water pH 0 added (mL) | Total volume (mL) | Crystals S-ee (%) | Crystals yield (%) |
|---|---|---|---|---|
| 3 | — | 23 | 99.82 | 65.38 |
| 4 | — | 24 | 99.76 | 73.06 |
| 5 | — | 25 | 99.68 | 79.10 |
| 6 | — | 26 | 90.99 | 86.96 |
| 7 | — | 27 | 85.88 | 92.36 |
| — | 1 | 21 | 99.89 | 59.85 |
| — | 2 | 22 | 99.79 | 72.25 |
| — | 3 | 23 | 99.70 | 76.58 |
| — | 4 | 24 | 96.71 | 81.84 |
| — | 5 | 25 | 91.67 | 85.54 |

As shown in Table 2, an increase in water and a decrease in pH both lowered the solubility of the desired compound. With a starting material having a 77.24% ee in S-isomer, conditions using 3 mL of a pH 0 solution offered the best result. Indeed, a near perfect 76.58% yield was obtained with >99% ee. Acidification at lower temperature (10-20° C.) was found preferable as it led to less side reactions and improved yields, compared a warmer (40-55° C.) acidification. These conditions (addition of about 15% water pH 0 to 69-70 g/L solution of compound) applied to the rest of the mother liquors (200 mL) proved robust enough to offer good returns on a 13.8 g scale. Indeed, 8.87 g of S-isomer with >99% ee were obtained after filtration and further drying (rotavap 5-10 mbars, 45° C., 4 h). $^{1}$H-NMR showed presence of 0.52 eq water.

Steps (a) and (b) were repeated using 500 g of racemic starting material, 208 g of (−)-quinine (0.65 eq.), and 3.48 kg MeCN (about 4.43 L) in step (a). Step (b) was performed as above using 270 g of S-isomer enriched compound (ee: 76.24%), MeCN (total volume 3.9 L) and 1N HCl (pH 0, 592 mL), and afforded 205 g of S-isomer (Formula II(a)) at 99.5 ee %. The compound can be used in the preparation of compounds of Formula III, for example Compounds 1, 7, 9, 11, 13, 15, 17, 19, 21, 23 and 25.

Example 4—R-Isomer Isolation and Racemisation (Formula I(a))

R-isomer rich crystals, for instance isolated from step (a) of Example 3, comprising the (−)-quinine salt of the R-isomer were recycled by first breaking the salt formed then by racemizing the isolated R-isomer for reuse in the resolution process. Two alternative processes are exemplified below.

Process 1:

The first step was carried out by mixing the salt (about 230 g (R), 140 g quinine) in 2.3 L of HPLC grade dichloromethane and adding 1.15 L of a 1N HCl solution under stirring. The mixture was mixed at 20° C. for 1.5 hour. The organic phase was separated, washed with 0.6 L of water, and dried over $MgSO_4$. Filtration and evaporation under reduced pressure afforded the R-isomers rich compound (211 g, 92% yield).

The solid obtained was then dissolved in anhydrous DME (1 L) and mixed with DBU (93.5 mL, 1.5 eq.). The solution was stirred at 70-80° C. for 6 hours. The mixture was cooled to 10-20° C. and water was added. The pH was adjusted to 4-5 by addition of HCl. The aqueous phase was extracted with ethyl acetate and the combined organic layers were washed with brine and dried with $MgSO_4$. All volatiles were removed under reduced pressure and the residue triturated with MTBE/EtOAc (8/1). The slurry was filtered and washed with cold MTBE. The solid was further dried under reduced pressure to afford the racemic compound of Formula I(a) (175 g, 82% yield). This racemic compound is then further used in the process of Example 3 to produce the S-isomer.

Process 2:

The R-isomer quinine salt (79 kg, 1.0 eq.) is introduced into the reaction vessel. A 1N hydrochloric acid solution (3 volumes) is added to the vessel followed by 2-methyltetrahydrofuran (2-MeTHF) (2 volumes) and the mixture is stirred until it becomes clear. The mixture is separated, and the organic phase is washed with water (1 volume) and concentrated to dryness. DME (3 volumes) is added, and the mixture is again concentrated to dryness.

The solid obtained was then dissolved in anhydrous DME (3 volumes) and mixed with DBU (1.5 eq.). The solution was stirred at 70-80° C. until complete racemization is achieved (monitored by chiral chromatography). The mixture was cooled to 10-20° C. and water (3.5 volumes) was added dropwise. The pH was adjusted to 2-3 by the dropwise slow addition of a 1N HCl solution. The mixture is filtered, and the cake is washed with water (2 volumes). The cake Is dried at 50-60° C. to afford the racemic compound of Formula I(a) (42 g, 95% yield). This racemic compound is then further used in the process of Example 3 to produce the S-isomer.

Example 5—Optical Resolution of the Compound of Formula I(b)

To a mixture of Compound of Formula I(b) (96.0 g, 1.00 eq.) in MeCN (960 mL) was added (−)-quinine (50.0 g, 0.76 eq.) at 15-20° C., and then the mixture was stirred at 60-70° C. for 1.5 hours. Then the mixture was cooled to 20-30° C. and stirred for 16 hrs. The mixture was filtered, the cake was dried to give white solid (96.0 g) which was check by SFC and HPLC. The mother liquor was checked by SFC and HPLC. The mother liquor was warmed to 40-45° C., to the solution was added HCl (1M, 61.7 mL) and $H_2O$ (150 mL). The mixture was stirred at 15-20° C. for 4 hours. The mixture was then filtered and a solid was obtained. The solid was triturated with $MeCN/H_2O$ (150 mL/15 mL). The S-isomer (25.0 g, 99.5% purity) of Formula II(b) was obtained as a light yellow solid, which was confirmed by $^1H$ NMR, LCMS, HPLC and SFC. The S-isomer can be further used in the preparation of compounds of Formula III, for instance in the preparation of Compounds 2, 8, 10, 12, 14, 16, 18, 20, 22, 24 and 26, or for the preparation of other compounds such as (S)-Ibipinabant and other compounds described in U.S. Pat. No. 9,765,031 and PCT Patent Applications No. WO2009/059264 and No. WO2014/018695.

$^1H$ NMR (400 MHz, DMSO-$d_6$) δ 11.60 (s, 1H), 7.93-8.10 (m, 2H), 7.80 (d, J=8.8 Hz, 2H), 7.67-7.76 (m, 2H), 7.37-7.52 (m, 2H), 7.26-7.36 (m, 2H), 7.12-7.26 (m, 3H), 4.98 (dd, J=11.6, 4.8 Hz, 1H), 4.27 (t, J=11.6 Hz, 1H), 3.67 (dd, J=11.2, 4.8 Hz, 1H). LCMS: RT=1.063 min, m/z=474 $(M+H)^+$.

Numerous modifications could be made to any of the embodiments described above without departing from the scope of the present invention. Any references, patents or scientific literature documents referred to in the present document are incorporated herein by reference in their entirety for all purposes.

We claim:

1. A process for preparing an enantiomerically enriched compound, comprising the steps of:

(a) providing a compound of Formula I(a) or I(b) or a tautomer thereof:

Formula I(a)

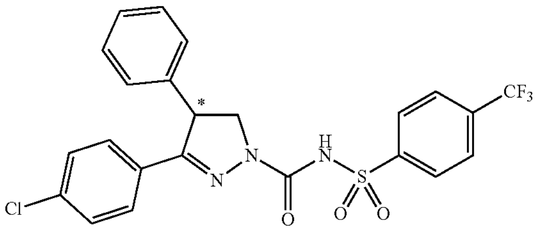 [SMILES: O=C(NS(=O)(=O)c1ccc(C(F)(F)F)cc1)N1CC(c2ccccc2)C(c2ccc(Cl)cc2)=N1]

Formula I(b)

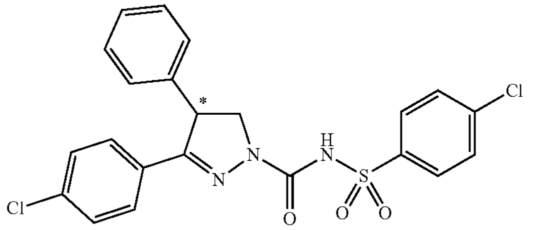

wherein said compound of Formula I(a) or I(b) comprises a mixture of R and S isomers at the (*) carbon atom (C*) and wherein the fourth atom attached to C* is hydrogen or an isotope thereof;

(b) dissolving the compound of Formula I(a) or I(b) in a solvent to obtain a solution;

(c) dissolving a chiral resolving agent selected from (−)-quinine, (R)-phenethylamine, (S)-phenethylamine, (S)-1-naphthylethylamine, (R)-(−)-2-amino-3-methyl-1-butanol, (−)-cinchonidine, (−)-spartein, (R)-1-naphthylethylamine, D-arginine, L-lysine, (S)-(+)-2-pyrrolidinemethanol, and (1R,2S)-(+)-cis-1-amino-2-indanol in the solution to form a precipitate and a supernatant; and (d) separating the precipitate from the supernatant, wherein one of the precipitate or the supernatant comprises the enantiomerically enriched compound comprising a higher concentration in S-enantiomer compared to the R-enantiomer of the compound of Formula I(a) or I(b);

wherein steps (b) and (c) are carried out simultaneously or sequentially.

2. The process of claim 1, wherein said solvent is acetonitrile.

3. The process of claim 1, wherein said solvent is selected from ethanol, isopropanol, and a combination thereof.

4. The process of claim 2, wherein said solvent further comprises water at a concentration of 10% or less or the solvent is anhydrous.

5. The process of claim 1, wherein the compound of Formula I(a) or I(b) is in a concentration of between 50 g and 150 g, per liter of solvent in step (b).

6. The process of claim 1, wherein step (c) comprises between 0.5 and molar equivalent of said chiral resolving agent with respect to the compound of Formula I(a) or I(b).

7. The process of claim 1, wherein said chiral resolving agent is selected from (−)-quinine, (R)-phenethylamine, (S)-phenethylamine, (S)-1-naphthylethylamine, and (R)-(−)-2-amino-3-methyl-1-butanol.

8. The process of claim 7, further comprising a step of treating the supernatant to obtain a solid enriched in(S) isomer of the compound of Formula I(a) or I(b).

9. The process of claim 8, wherein said step of treating comprises concentrating the supernatant by at least partial evaporation of the solvent.

10. The process of claim 8, wherein said step of treating comprises adding an acidic aqueous solution to the supernatant.

11. The process of claim 10, wherein the acidic aqueous solution has a pH comprised within the range of 0 to 1 and the volume ratio of the acidic aqueous solution to the total volume of solution is between 4% and 20%.

12. The process of claim 11, wherein the acidic aqueous solution has a pH of 0, and the volume ratio of the acidic aqueous solution to the total volume of solution is between 10% and 16%.

13. The process of claim 8, further comprising a step of separating the solid from the supernatant.

14. The process of claim 1, wherein said chiral resolving agent is selected from (−)-cinchonidine, (−)-spartein, (R)-1-naphthylethylamine, D-arginine, L-lysine, (S)-(+)-2-pyrrolidinemethanol, and (1R,2S)-(+)-cis-1-amino-2-indanol.

15. The process of claim 14, further comprising recrystallizing the precipitate.

16. The process of claim 1, further comprising a step of separating the(S) isomer of the compound of Formula I(a) or I(b) from the chiral resolving agent.

17. The process of claim 16, wherein said step of separating comprises adding hydrochloric acid.

18. The process of claim 1, further comprising recovering the (R) isomer of the compound of Formula I(a) or I(b), at least partially racemizing said (R) isomer to obtain the compound of Formula I(a) or I(b), and further treating said compound by steps (a) to (d).

19. The process of claim 1, wherein said solvent is isopropanol.

20. The process of claim 2, wherein said solvent further comprises water at a concentration of 5% or less or the solvent is anhydrous.

21. The process of claim 1, wherein the compound of Formula I(a) or I(b) is in a concentration of between 75 g and 120 g per liter of solvent in step (b).

22. The process of claim 1, wherein the compound of Formula I(a) or I(b) is in a concentration of between 85 g and about 115 g per liter of solvent in step (b).

23. The process of claim 1, wherein step (c) comprises between 0.55 and 0.75 molar equivalent of said chiral resolving agent with respect to the compound of Formula I(a) or I(b).

24. The process of claim 1, wherein step (c) comprises between 0.6 and 0.7 molar equivalent of said chiral resolving agent with respect to the compound of Formula I(a) or I(b).

25. The process of claim 1, wherein step (c) comprises 0.65 molar equivalent of said chiral resolving agent with respect to the compound of Formula I(a) or I(b).

26. The process of claim 11, wherein the acidic aqueous solution has a pH of 0, and the volume ratio of the acidic aqueous solution to the total volume of solution is between 12% and 14%.

27. The process of claim 1, wherein said chiral resolving agent is (−)-quinine.

28. The process of claim 1, wherein said chiral resolving agent is (−)-spartein.

* * * * *